(12) United States Patent
Cauthen

(10) Patent No.: US 6,679,915 B1
(45) Date of Patent: Jan. 20, 2004

(54) ARTICULATING SPINAL IMPLANT

(75) Inventor: Joseph C. Cauthen, Gainesville, FL (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/513,954

(22) Filed: Feb. 28, 2000

Related U.S. Application Data

(63) Continuation-in-part of application No. 09/389,758, filed on Sep. 2, 1999, now Pat. No. 6,440,168, which is a continuation-in-part of application No. 09/298,524, filed on Apr. 23, 1999, now Pat. No. 6,179,874, which is a continuation-in-part of application No. 09/065,816, filed on Apr. 23, 1998, now Pat. No. 6,019,792.

(51) Int. Cl.$^7$ .................................................. A61F 2/44

(52) U.S. Cl. ................... 623/17.11; 623/17.14
(58) Field of Search ................... 623/17.11–17.16, 623/17

(56) References Cited

U.S. PATENT DOCUMENTS

| | | |
|---|---|---|
| 4,011,602 A | 3/1977 | Rybicki et al. |
| 4,309,777 A | 1/1982 | Patil |
| 4,349,921 A | 9/1982 | Kuntz |
| 4,484,570 A | 11/1984 | Sutter et al. |
| 4,501,269 A | 2/1985 | Bagby |
| 4,553,273 A | 11/1985 | Wu |
| 4,595,663 A | 6/1986 | Krohn et al. |
| RE32,449 E | 6/1987 | Claussen et al. |
| 4,714,469 A | 12/1987 | Kenna |
| 4,759,766 A | 7/1988 | Buettner-Janz et al. |
| 4,759,769 A | 7/1988 | Hedman et al. |
| 4,772,287 A | 9/1988 | Ray et al. |
| 4,863,476 A | 9/1989 | Shepperd |
| 4,932,969 A | 6/1990 | Frey et al. |
| 4,932,975 A | 6/1990 | Main et al. |
| 4,936,848 A | 6/1990 | Bagby |
| 4,946,378 A | 8/1990 | Hirayama et al. |
| 4,961,740 A | 10/1990 | Ray et al. |
| 4,997,432 A | 3/1991 | Keller |
| 5,002,576 A | 3/1991 | Fuhrmann et al. |
| 5,015,247 A | 5/1991 | Michelson |

(List continued on next page.)

FOREIGN PATENT DOCUMENTS

| | | | |
|---|---|---|---|
| EP | 0042271 | 12/1981 | |
| EP | 0640326 | 3/1995 | |
| EP | 0 716 840 | 12/1995 | |
| EP | 0716840 | 6/1996 | |
| WO | 9214423 | 9/1992 | |
| WO | 9310725 | 6/1993 | |
| WO | WO 94/07441 | 8/1993 | |
| WO | 9814142 | 4/1998 | |
| WO | WO 99/11203 A | * 3/1999 | ............. A61F/2/44 |
| WO | WO 99/53871 | 10/1999 | |

OTHER PUBLICATIONS

Krames Communications, Neck Owner's Manual, 1985, all pages.

Cauthen et al. (1998) "Outcome Analysis of Noninstrumented Anterior Cervical Discetomy and Interbody Fusion in 348 Patients" *SPINE* 23(2):188–192.

(List continued on next page.)

Primary Examiner—David H. Willse
(74) Attorney, Agent, or Firm—Woodard, Emhardt, Moriarty, McNett & Henry LLP

(57) ABSTRACT

An articulating spinal implant for intervertebral disc replacement. The articulating spinal implant is formed from two elements, each engaging one of an adjacent pair of vertebra. Articulation features between the two elements resist compression and lateral movement between the vertebra, but allow the adjacent vertebra to articulate about an instantaneous axis of rotation.

27 Claims, 12 Drawing Sheets

U.S. PATENT DOCUMENTS

| | | | |
|---|---|---|---|
| 5,037,438 A | | 8/1991 | Davidson |
| 5,236,460 A | | 8/1993 | Barber |
| 5,258,031 A | | 11/1993 | Salib et al. |
| 5,306,307 A | | 4/1994 | Senter et al. |
| 5,306,308 A | | 4/1994 | Gross et al. |
| 5,314,477 A | | 5/1994 | Marnay |
| 5,401,269 A | | 3/1995 | Buttner-Janz et al. |
| 5,425,773 A | | 6/1995 | Boyd et al. |
| 5,489,308 A | | 2/1996 | Kuslich et al. |
| 5,545,229 A | | 8/1996 | Parsons et al. |
| 5,562,738 A | * | 10/1996 | Boyd et al. ............... 623/17.15 |
| 5,593,445 A | | 1/1997 | Waits |
| 5,725,590 A | | 3/1998 | Maumy et al. |
| 5,735,901 A | | 4/1998 | Maumy et al. |
| 6,039,763 A | * | 3/2000 | Shelokov ................. 623/17.16 |

OTHER PUBLICATIONS

The American Association of Neurological Surgeons Understanding Problems with Your Cervical Spine (1996) Centrax Bipolar System Simple & Complete. How Medica (1988, 1993).

Bioreabsorable Implants Applications in Anterior Cruciate Ligament Reconstruction (Author & date unknown).

You Have Questions About Bioabsorable Implants? Instrument Makar, Inc. (date unknown).

Bao & Yuan, The Artificial Disc, Science & Medicine Jan./Feb., 1998, vol. 5, No. 1.

Qi–Bin Bao et al. (1996) "The Artificial Disc: Theory, Design and Materials" *Biomaterials* 17(12).

A Guide to the Care and Treatment of Common Neck Problems, Neck Owner's Manual, Krames Comm. (1981–1984).

Treating Neck and Arm Pain and Weakness "Cervical Disk Surgery" Krames Comm. (1990).

* cited by examiner

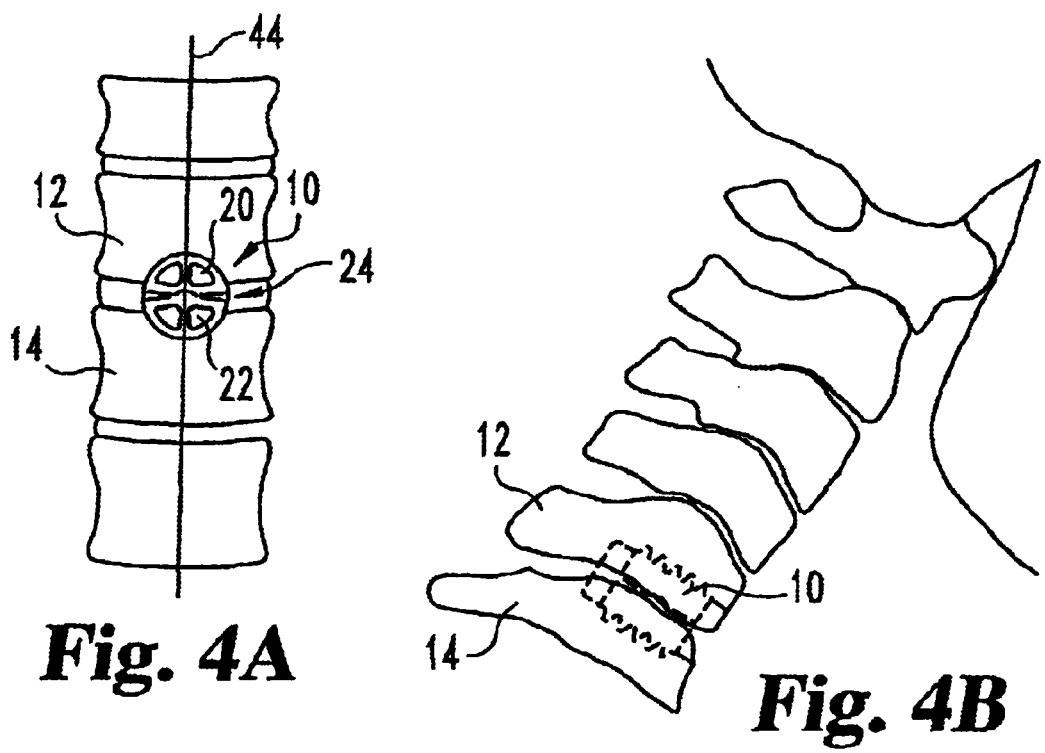
Fig. 4A
Fig. 4B
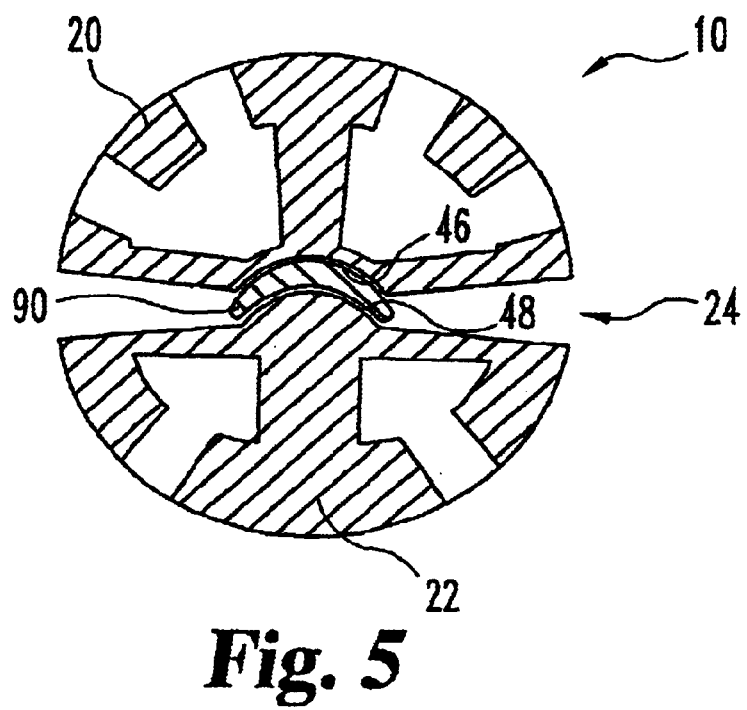
Fig. 5

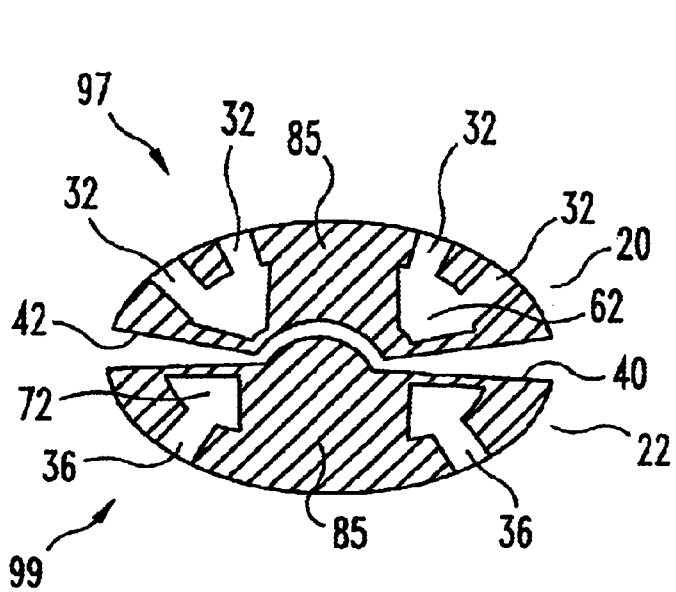 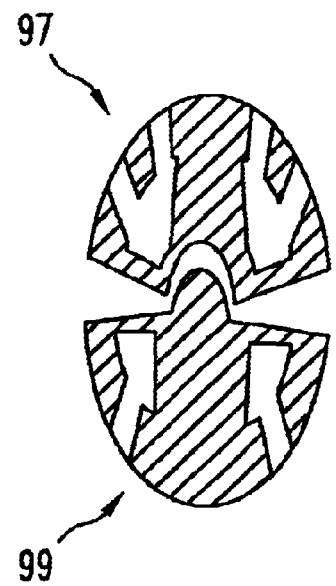
Fig. 6A   Fig. 6B
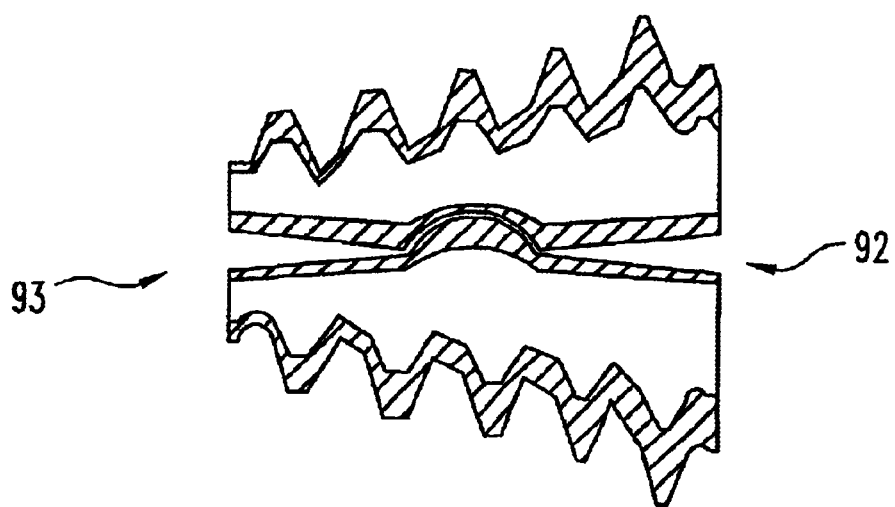
Fig. 7

ARTICULATING SPINAL IMPLANT

CROSS-REFERENCE TO A RELATED APPLICATION

This application is a continuation-in-part of patent application Ser. No. 09/389,758, filed Sep. 2, 1999, now U.S. Pat. No. 6,440,168, which is a continuation-in-part of patent application Ser. No. 09/298,524, filed Apr. 23, 1999, now U.S. Pat. No. 6,179,874, which is a continuation-in-part of patent application Ser. No. 09/065,816, filed Apr. 23, 1998, now issued on Feb. 1, 2000 as U.S. Pat. No. 6,019,792.

BACKGROUND OF THE INVENTION

1. Field of the Invention

The invention relates generally to spinal implants for use in intervertebral disc replacement; and more specifically relates to articulating implants that fuse to adjacent vertebra by bone ingrowth, thus restoring proper intervertebral spacing, and eliminating nerve root and/or spinal cord compression, while preserving spinal flexibility.

2. Description of Related Art

The spinal column is formed from a number of vertebra, which in their normal state are separated from one another by cartilaginous intervertebral discs. These discs form a cushion between adjacent vertebra, resisting compression along the support axis of the spinal column, but permitting limited movement between the vertebra to provide the characteristic flexibility of the healthy spine. Injury, disease or other degenerative disorders may cause one or more intervertebral discs to shrink, collapse, deteriorate or become displaced, herniated, or otherwise damaged. This can lead to compression of adjacent nerve root(s) or the spinal cord causing chronic and often disabling pain, and in advanced circumstances, irreversible paralysis of upper and/or lower limbs.

A number of devices and methods have been suggested for the replacement of damaged or dislocated intervertebral discs. One common approach is to permanently stabilize or "fuse" the adjacent vertebra to maintain the proper intervertebral spacing and eliminate relative movement between the vertebra. Various methods of vertebral stabilization have been developed, for example, autogenous grafts of dowel-shaped sections of bone have been implanted between the vertebra to cause bone growth across the intervertebral space, thereby fusing the adjacent vertebra into one bone mass. This procedure disadvantageously requires the harvest of donor bone for the graft from other parts of the patient's body, typically requiring a separate surgical procedure and resultant increases in complications and expense. An alternative source is cadaver bone, with potential complications of transmissible diseases, impaired graft incorporation, collapse or displacement. A further development to this method of vertebral stabilization involves the implantation of a perforated cylindrical bone basket between adjacent vertebra. Bone fragments produced in preparing the vertebra for the implantation are inserted into the bone basket to promote bone growth into, through, and around the basket.

Vertebral stabilization by fusion of adjacent vertebra has proven successful in permanently preserving intervertebral spacing, but has been found to present a number of disadvantages. Fusion of adjacent vertebra necessarily eliminates a portion of the spine's normal range of motion, thereby reducing the subject's spinal flexibility. Additionally, long-term investigations after fusion of the vertebra have revealed deterioration in the next adjacent segments, ranging from increasing osteophyte formation, to collapse of the intervertebral disc, implicating progressive degeneration of the afflicted motion segment, resulting in hyper- and/or hypo-mobility of the segment. It is believed that fusion results in nonphysiological bio-mechanical stress of the adjacent segment. In addition to the nonphysiological bio-mechanical stress, there is an increase in the intradiscal pressure (PID) on the adjacent intervertebral disc. Changes in the PID may impair the nutrition of the intervertebral disc, which can lead to increased degeneration and pain in any plane of motion and/or compression of the spinal cord on spinal nerves.

It has also been proposed to replace an injured intervertebral disc with a prosthesis which is "jointed" to permit relative movement between vertebra. Previously known devices of this type generally have been found to suffer from inadequate attachment between the prosthesis and the vertebra. The intended movement between the components of previously known jointed prostheses can cause relative motion between the prosthesis and the adjacent bone surface(s). Because such motion would disrupt bone ingrowth, jointed prostheses have generally been considered incompatible with attachment by bone ingrowth. In addition, because the joint elements of these devices typically must occupy a substantial vertical extent in order to achieve the desired range of motion, and yet must fit within the intervertebral space, attachment of such devices generally has been by use of flat plates or surfaces provided on either side of the joint elements as points of fixation to the vertebra. This attachment may be accomplished by compressive or friction fits, spiked projections, screws or pins, complemented in some instances with tissue ingrowth into porous surfaces. These mechanisms of attachment, however, may lack the degree and strength of fixation desired. Moreover, several such devices have used attachment flanges which extend beyond the surfaces of the vertebra to which the device is attached. This has been found undesirable, as the extending flanges may interfere with or injure adjacent tissue; for example, it has been reported that flanges extending into immediately adjacent delicate esophageal areas may interfere with swallowing and speech, or cause perforation and potentially fatal infection. An additional drawback to the use of screw and pin connections is the potential for such connectors to dislodge and cause injury. Examples of such prosthetic implants are disclosed in the following: U.S. Pat. No. 4,759,769, to Hedman et al., U.S. Pat. No. 4,946,378, to Hirayama et al., U.S. Pat. No. 4,997,432, to Keller, U.S. Pat. No. 5,002,576, to Fuhrmann et al., U.S. Pat. No. 5,236,460, to Barber, U.S. Pat. No. 5,258,031, to Salib et al., U.S. Pat. No. 5,306,308, to Gross, et al., U.S. Pat. No. 5,401,269, to Buttner-Janz, et al., U.S. Pat. No. 5,425,773, to Boyd, et al. and U.S. Pat. No. 5,782,832, to Larsen, et al.

Thus, it can be seen that a need yet exists for a spinal implant effective in permanently maintaining intervertebral spacing to prevent nerve or spinal cord compression, while preserving as much of the natural range of motion between the affected vertebra as possible. A need further exists for such a device which is capable of forming a permanent, strong attachment to the vertebra, yet does not protrude beyond the external surfaces to which it is attached. Still another need exists for a method of replacing a damaged or displaced disc, maintaining intervertebral spacing to prevent nerve and spinal cord compression, while preserving the natural relative motion between the vertebra. It is to the provision of devices and methods meeting these and other needs that the present invention is primarily directed.

BRIEF SUMMARY OF THE INVENTION

Briefly described, in a preferred form, the present invention comprises a spinal implant including a first element having first connection means for engaging a first vertebra. The first connection means includes a first fusion chamber having at least one opening therein for facilitating bone ingrowth into the first fusion chamber to fuse the first element to the first vertebra. The implant also includes a second element having second connection means for engaging a second vertebra. The second connection means includes a second fusion chamber having at least one opening therein for facilitating bone ingrowth into the second fusion chamber to fuse the second element to the second vertebra. The implant also includes internal articulation means, coupling the first element to the second element, for allowing relative movement between the first element and the second element. As used herein, the term "internal articulation means," refers to a means for facilitating relative motion between components of the implant, rather than between the implant and an external structure such as adjacent bone or other tissue.

In specific embodiments of the subject invention, the first and second elements may have either hemi-cylindrical or hemi-elliptical shaped outer surfaces. The first and second elements each having an outer wall perforated with one or more openings provided therein to allow bone ingrowth into the fusion chambers, and having abutting joint surfaces forming the internal articulation means. In a further preferred embodiment, the joint surfaces are formed as engaging concave and convex surfaces to create a ball-and-socket type joint (or rocker and channel, or other such joint), which allows relative pivotal motion between the vertebra, but resists compression there between.

The first and second elements can join to form a single element which can be implanted using methods similar to those followed in the implantation of previously known non-articulating vertebral fusion implants. Temporary stabilizing means can be provided for rigidly coupling the first and second elements by interposition of bioreabsorbable elements to permit implantation and enable bone ingrowth into the fusion chambers and fusion of the first and second elements to adjacent bone during an initial stabilization period, after which said temporary means biodegrades permitting articulation between the first and second elements.

The present invention can be further described as comprising a spinal implant having a first articulation surface, a second articulation surface engaging at least a portion of the first articulation surface along a support axis generally parallel to the spinal column, first connection means for connecting the first articulation surface to a first vertebra, and second connection means for connecting the second articulation surface to a second vertebra. The first and second articulation surfaces resist axial compression between the first and second elements in the direction of the support axis, but allows relative pivotal motion between the first and second elements. At least one, and preferably both, of the first connection means and the second connection means comprise a fusion chamber having at least one opening therein for facilitating bone ingrowth, thereby permanently and securely affixing the implant in place.

In another preferred form, the present invention comprises a method of maintaining an intervertebral space between a first vertebra and a second vertebra. The method includes the steps of removing a section of the first vertebra to form a cavity therein, mounting a first element of a spinal implant within the cavity formed in the first vertebra, and connecting a second element of the spinal implant to the second vertebra. The first element includes a first articulation surface and a first fusion chamber having at least one opening therein for facilitating bone ingrowth from the first vertebra. The second element includes a second articulation surface, wherein the first and second articulation surfaces adjoin to form a joint allowing relative pivotal movement between the first and second elements but preventing relative compression between the first and second elements. In a further preferred embodiment, the method may also include the removal of a section of the second vertebra to form a cavity for receiving the second element. The second element may also include a second fusion chamber for facilitating bone ingrowth from the second vertebra. Bone fragments formed by the removal of vertebral sections to accommodate implantation or bone growth stimulating compounds or devices may be inserted into the fusion chamber(s) to enhance bone ingrowth.

These and other objects, features and advantages of the present invention, will be more readily understood with reference to the following detailed description, read in conjunction with the accompanying figures. All patents, patent applications and publications referred to or cited herein, or from which a claim for benefit of priority has been made, are incorporated by reference in their entirety to the extent they are not inconsistent with the explicit teachings of this specification.

BRIEF DESCRIPTION OF THE FIGURES

FIG. 4a is an end view of a spinal implant in situ according to the cylindrical form of the present invention.

FIG. 4b is a side view of a spinal implant in-situ according to the cylindrical form of the present invention.

FIG. 5 is a cross-sectional end view of another embodiment of the present invention showing an interposed bowl-shaped cap providing impact resistance and wear resistance.

FIG. 6a shows a cross-sectional end view of an elliptically-shaped spinal implant of the subject invention.

FIG. 6b shows a cross-sectional end view of an alternative elliptically-shaped spinal implant of the subject invention.

FIG. 7 shows a cross-sectional side view of the tapered spinal implant.

DETAILED DISCLOSURE OF THE INVENTION

Figure 1A:
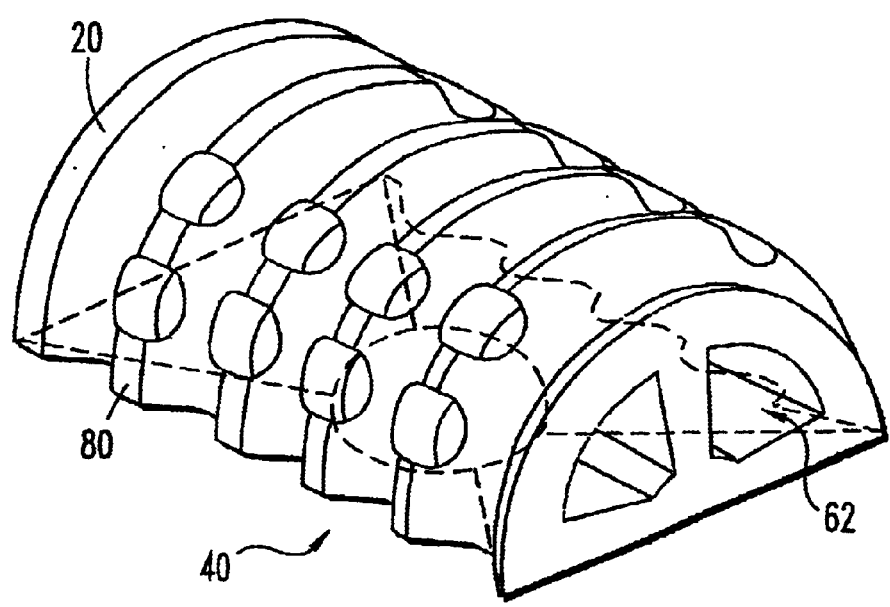
FIGS. 1a & 1b shows a perspective view of a spinal implant according to one cylindrical form of the present invention.
Figure 1B:
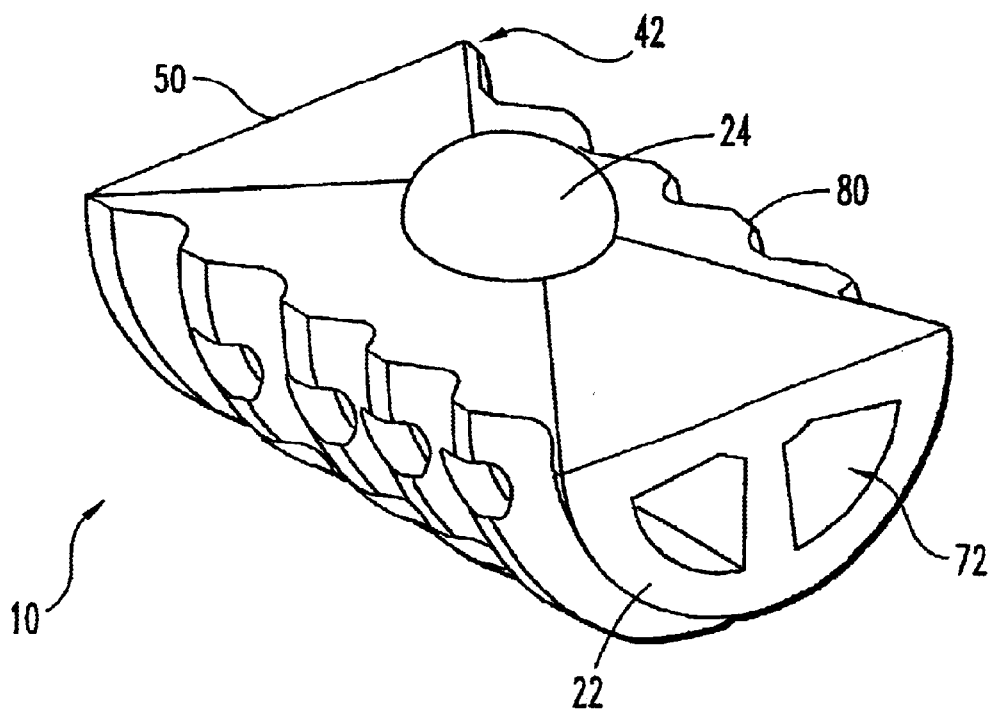
Figure 2:
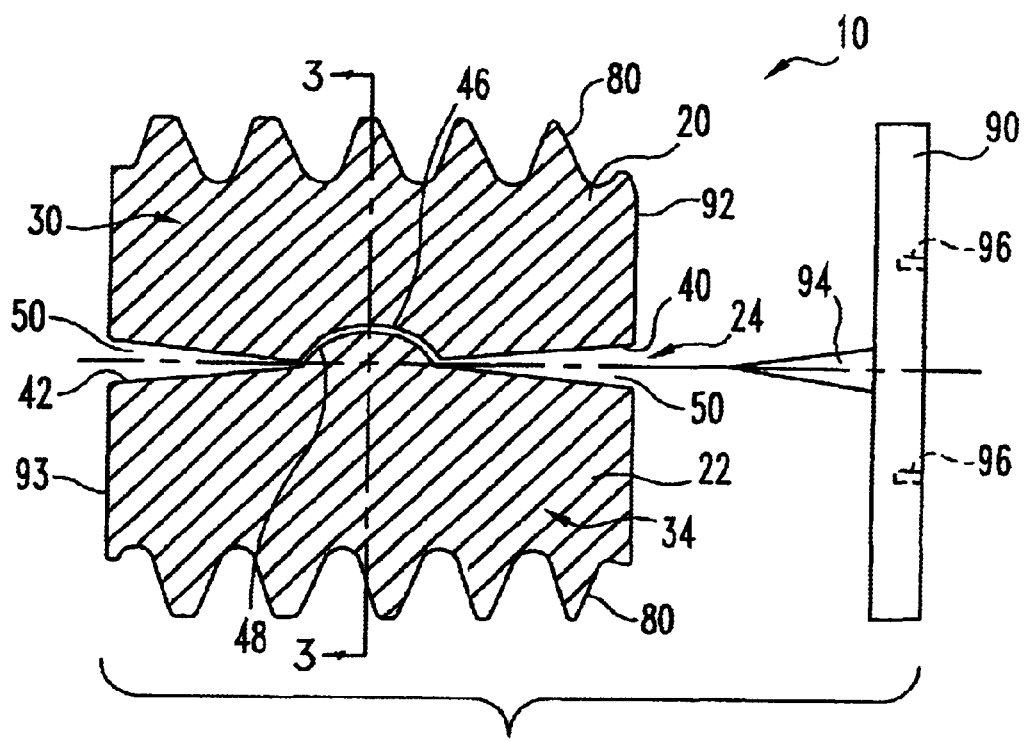
FIG. 2 shows a cross-sectional side view of the spinal implant of FIG. 1.
Figure 3:
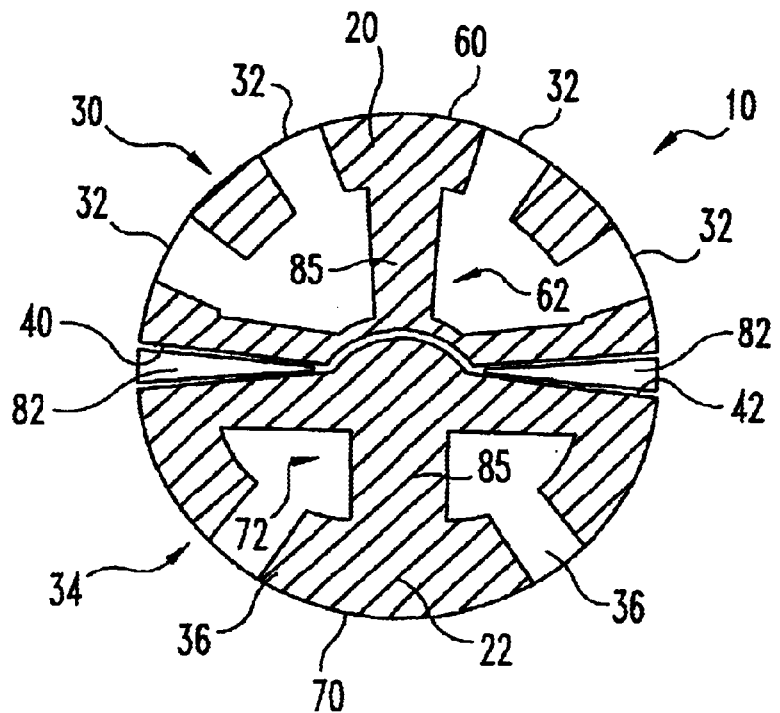
FIG. 3 shows a cross-sectional end view of the spinal implant of FIG. 1.

Referring now in detail to the figures, wherein like reference numbers represent like parts throughout, preferred forms of the present invention will now be described. As seen in FIGS. 1–3, one embodiment of the present invention comprises a spinal implant 10, generally comprising a first element 20 and a second element 22. The first element 20 is coupled to the second element 22 by an internal articulation means 24 for allowing relative pivotal movement between the first and second elements.

FIGS. 4A and 4B show the spinal implant 10 of the present invention installed in situ, between a first vertebra 12 and a second vertebra 14. The implant 10 is shown implanted into an anterior aspect of the vertebral body, between the fifth cervical and sixth cervical vertebra. The device and method of the present invention, however, are applicable to anterior, lateral, and posterior approaches to the vertebra.

As seen best in FIGS. 2–3, the first element 20 of the implant 10 comprises first connection means, in the form of a first fusion chamber 30, for engaging the first vertebra 12. At least one opening 32 is formed in the first fusion chamber 30, to facilitate bone growth into, through and around the first fusion chamber 30 from the first vertebra 12, to fuse the first element to the first vertebra 12. Preferably, a plurality of openings 32 are provided to further promote bone ingrowth. Fusion by bone ingrowth has been found to provide a more permanent, rigid connection between the implant 10 and the skeletal structure, than provided by other known connection means.

The second element 22 of the implant 10 comprises a second connection means for engaging the second vertebra 14. The second connection means preferably comprises a second fusion chamber 34, substantially similar in construction to the above-described first fusion chamber 30, and comprising at least one opening 36 formed therein for facilitating bone growth into, through, and around the second fusion chamber 34 from the second vertebra 14. Alternatively, the second connection means can comprise an adhesive connection, screw connection, pin connection, or any other effective alternative connection means. However, the provision of a second fusion chamber 34 is preferred, as it provides a more permanent and secure coupling than other known attachment means. Although the first element 20 and first vertebra 12 are depicted in the figures as above the second element 22 and second vertebra 14, it will be understood that the present invention equally comprehends the reverse configuration wherein the first element, as described herein, is attached to a first vertebra lower on the spinal column than the second vertebra to which is attached the second element. The first and second elements can be fabricated from biocompatible materials including, without limitation, titanium, surgical alloys, stainless steel, chrome-molybdenum alloy, cobalt chromium alloy, zirconium oxide ceramic, non-absorbable polymers and other anticipated biocompatible metallic or polymeric materials.

Referring now to FIGS. 2–3, the articulation means 24 of the present invention preferably comprises a first articulation surface 40 provided on the first element 20, and an abutting second articulation surface 42 provided on the second element 22. The first and second articulation surfaces 40, 42 are preferably fabricated from or coated with low-friction, wear and impact-resistant, biocompatible materials, such as, for example, titanium, stainless steel, surgical alloys, chrome-molybdenum alloys, cobalt chromium alloy, zirconium oxide ceramic, non-absorbable polymers and other biocompatible metallic or polymeric materials. The articulation means 24 resists axial compression between the first and second elements 20, 22, but allows relative pivotal movement there between. Thus, when implanted, as shown in FIG. 4, the articulation means 24 resists axial compression between first and second vertebra 12, 14 along a support axis 44 extending generally along the spinal column, as shown, for example, in FIG. 4, but permits pivotal movement between vertebra. The term "pivotal," is intended to comprehend either or both of a rotational or twisting motion about the support axis 44 (for example, rotation between cervical vertebra by turning the head to the right or left), and/or a tilting motion angularly inclined in any direction relative to the support axis 44 (for example, nodding the head forward or backward and/or tilting the head downward to the right or left).

In a preferred embodiment, axial compression, as well as lateral translation normal to the support axis 44, is resisted between the first and second vertebra 12, 14, by providing the first internal articulation surface 40 with a void, such as a concave surface 46, which receives a protuberance, such as a convex surface 48, projecting from the second internal articulation surface 42. This "ball-and-socket" arrangement allows relative rotation about the support axis 44 between the first and second vertebra 12, 14. The articulation means 24 can be provided with one or more stops to limit the range of rotational movement allowed.

Figure 16:
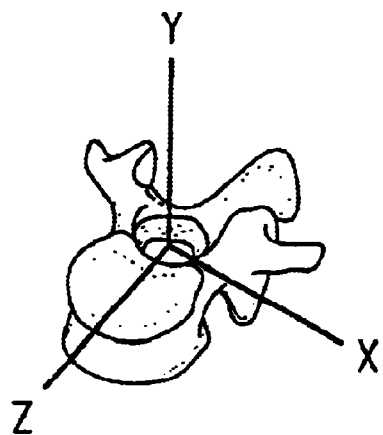
FIG. 16 shows a perspective view of a spinal motion segment displaying the Cartesian x, y, and z axes.
Figure 17:
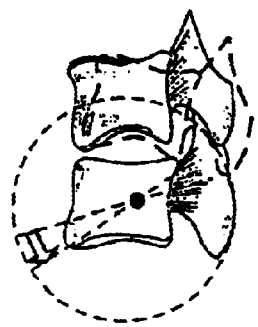
FIG. 17 shows a spinal motion segment comprising two adjacent vertebral bodies and an interposed intervertebral disc rotating about an instantaneous axis.
Figure 18A:
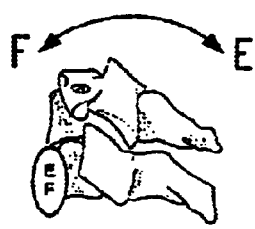
FIGS. 18*a*–18*c* show an instantaneous axis of rotation below the level of the intervertebral disc of a spinal motion segment in extension/flexion (E, F), right tilt/left tilt (R,L), and right rotation/left rotation (R,L) for various planes.
Figure 18B:
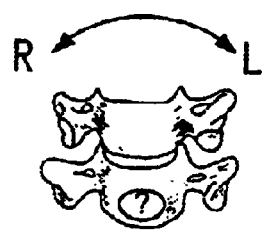
Figure 18C:
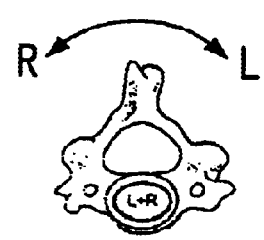

In addition to the "ball-and socket" arrangement for the articulating means 24, other configurations are possible which more closely follow the bio-mechanical motions of the first and second vertebra. The instantaneous motion of the first and second vertebra can be defined using the instantaneous axis of rotation. At every instant for a rigid body in plane motion, there is a line in the body or a hypothetical extension of this line that does not move. The instantaneous axis of rotation is this line. Plane motion is fully defined by the position of the instantaneous axis of rotation and the magnitude of the rotation about it. The resultant actions of the elementary movements between pairs of adjacent vertebra are the movements of flexion and extension. As shown in FIG. 17, the displacement of flexion-extension can be described as a circular movement about a transverse axis, where the axis is not situated at the level of the nucleus pulposus but lies below, in the body of the lower vertebra. The cartilage-lined articular facets produce an articular interface inscribed on the arc of a circle with the same center. The superior surface of the disc is also inscribed on an arc with the same center. The movement of the upper vertebra thus describes an arc with arcuate sliding of the articular facets and pendulous displacement of the disc about the same geometric center, known as the instantaneous axis of rotation. The instantaneous motion of a rigid body in three-dimensional space can be described as the resultant of the three rotations about the x, y and z axes, as shown in FIG. 16. As shown in FIGS. 18*a*–18*c*, the center varies during a given movement and describes an area comprising the instantaneous axis of rotation.

The location of the instantaneous axis of rotation may vary according to the region of the spine, for example, in the case of the C2–C3 articulation in the cervical spine, the instantaneous axis of rotation is geometrically lower then other centers in the cervical spine and is found in the body of C4. Below the C2–C3 intervertebral joint, the instantaneous axis of rotation of each cervical intervertebral articulation lies in the inferior part of the lower vertebra. In the thoracic and lumbar regions, the instantaneous axis of rotation is located in the central part of the superior surface of the lower vertebra. One consequence of this lower position of the instantaneous axis or rotation in flexion/extension is the anterior sliding or anterolisthesis of one superior or upper vertebra in the subjacent vertebra during extension.

Figures 19A, 19B, 19C:
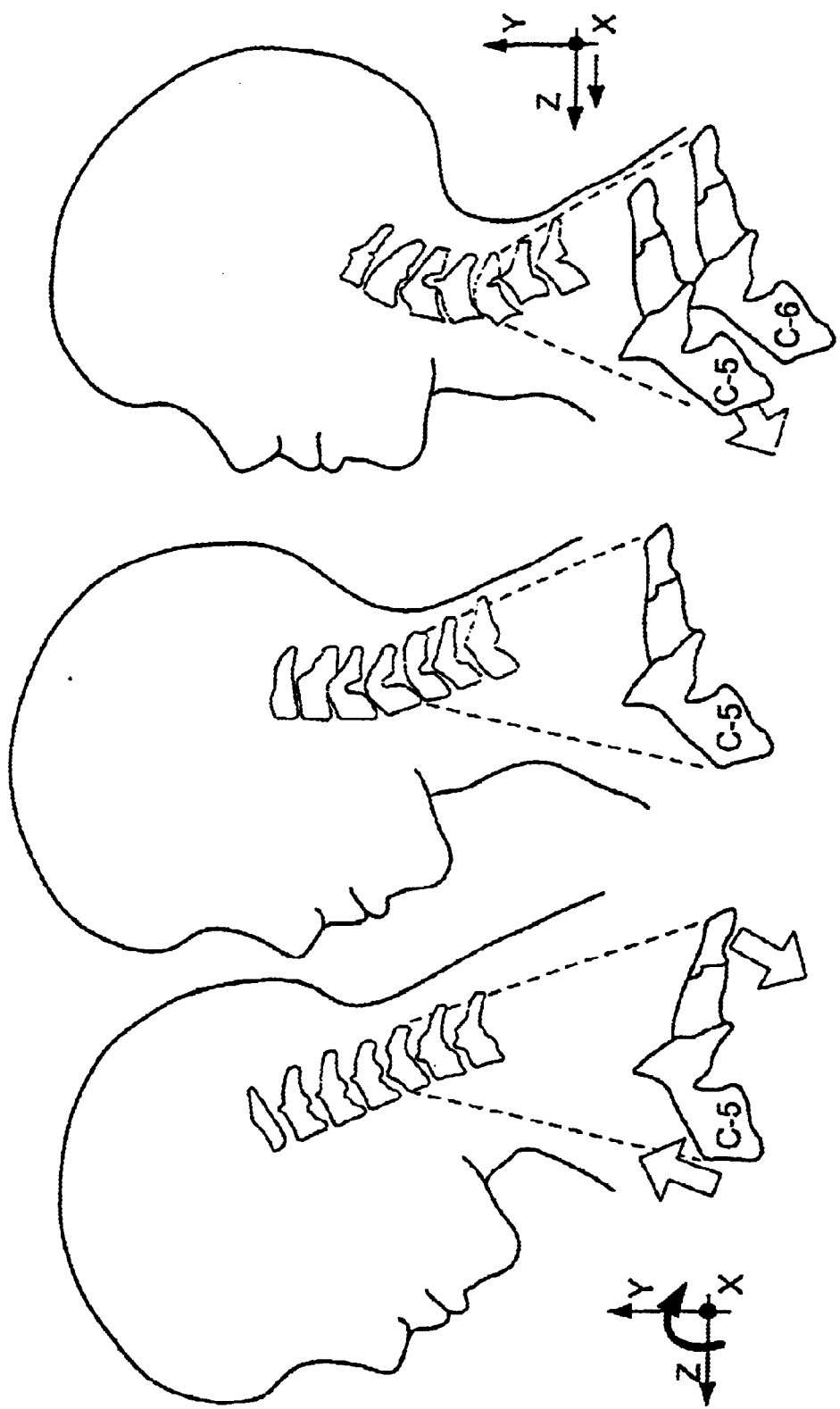
FIGS. 19*a*–19*c* show cervical spinal motion segments in flexion, neutral and extension.

This unexpected sliding movement is termed paradoxical motion. In paradoxical motion a functional spinal unit rotates in extension when the overall motion of the segment is in flexion. As shown in FIG. 19a, the functional spinal unit is in flexion, yet an unexpected (−x axis) rotation of the C5 vertebra occurs, a movement that would be expected if the functional spinal unit were in extension. The converse also occurs with extension. As shown in FIG. 19c, the functional spinal unit is in extension and a posterior (−z axis) translation is expected, yet the C5 vertebra displays an anterior (+z axis) translation. These paradoxical motions are described in the sagittal plane; they could also occur in the frontal and horizontal planes as well. An objective of the subject invention is a spinal implant which permits a first vertebra and second vertebra to articulate about an instantaneous axis of rotation and display paradoxical motion, where the articulation of the first vertebra and second vertebra is substantially similar to the physiological motion of a substantially identical pair of adjacent vertebrae interacting with a natural intervertebral disc.

Figure 8:
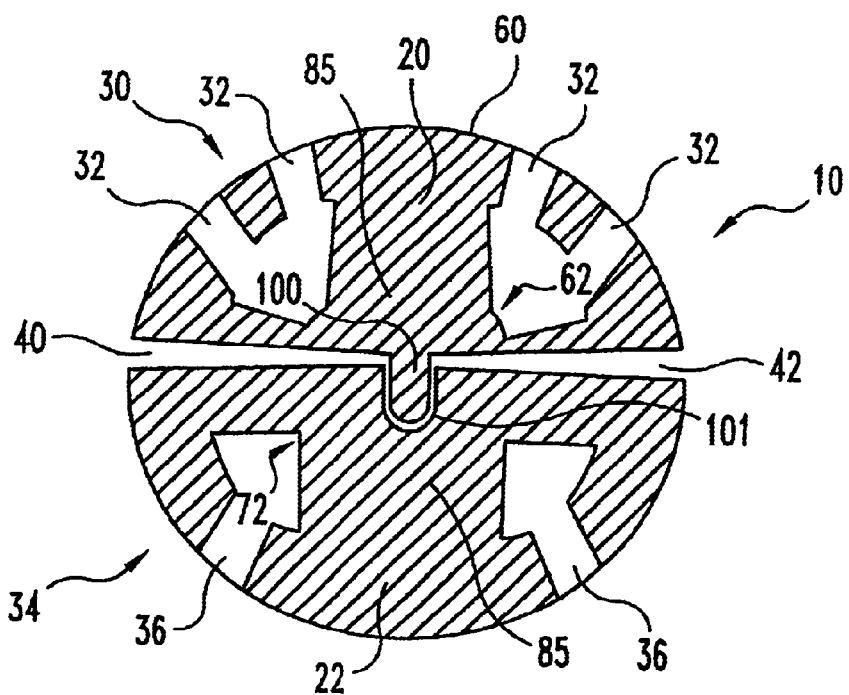
FIG. 8 shows a cross-sectional end view of a spinal implant with a rocker and channel articulating means.
Figure 10A:
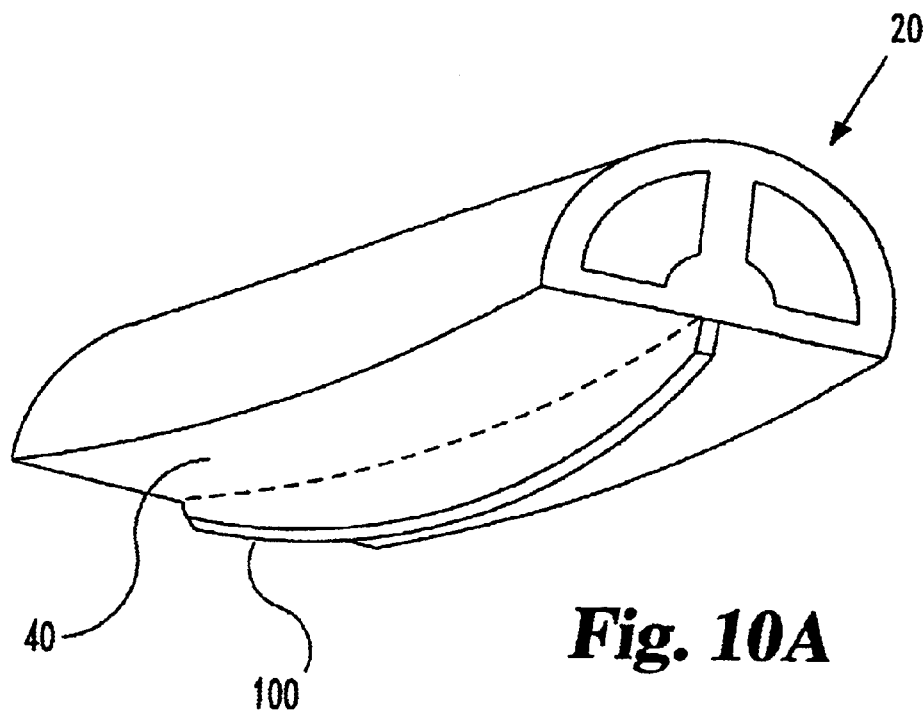
FIGS. 10a & 10b show a perspective view of a spinal implant with a rocker and channel articulating means.
Figure 10B:
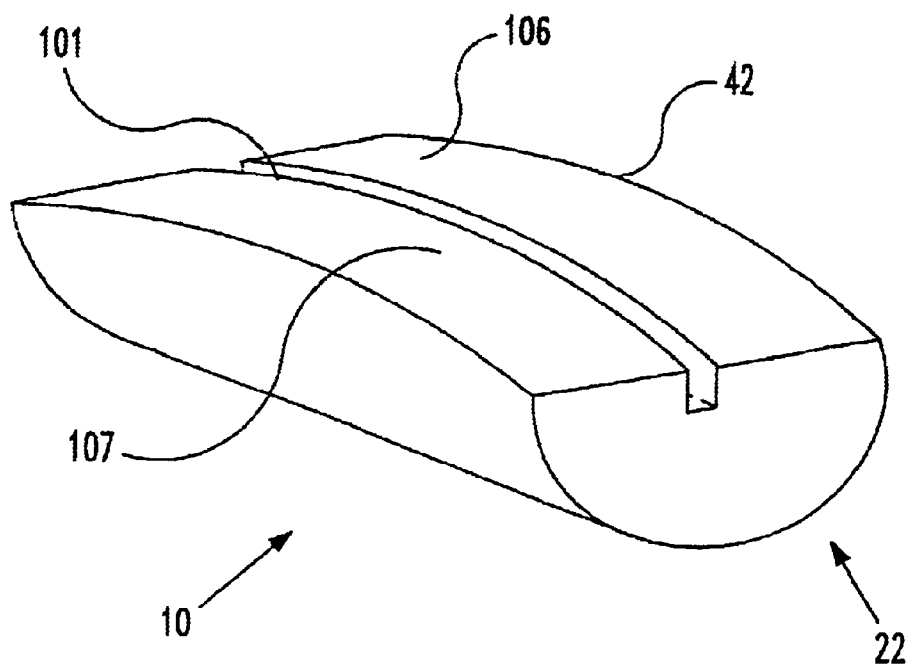

An example of a spinal implant with an articulating means which permits the first vertebra and second vertebra to articulate about an instantaneous axis of rotation and display paradoxical motion is shown in FIGS. 8, 10a and 10b, where the articulating means comprises a rocker 100 and channel 101. The second articulation surface 42 can comprise a substantially U-shaped channel 101 extending along the length of the second element 22. The first articulation surface 40 comprises a correspondingly shaped rocker 100 which can be, for example, hemi-elliptical in shape along the length of the first element 20. The rocker 100 and channel 101 articulating means simulate the physiological spinal articulating conditions of a vertebral disc during flexion and extension by allowing the first and second vertebra to rotate about an instantaneous axis, as shown in FIG. 17, and display paradoxical motion. Additionally, by increasing the number of ranges of motion, the spinal implant can rotate about an instantaneous axis and display paradoxical motion in the frontal and horizontal planes as well. Furthermore, by allowing the first and second vertebra to rotate about an instantaneous axis, the rocker 100 and channel 101 articulating means 24 can decrease the progressive degeneration of adjacent intervertebral discs by decreasing the nonphysiological bio-mechanical stresses and reducing the increase in intradiscal pressures normally associated with vertebral fusion.

Figure 9:
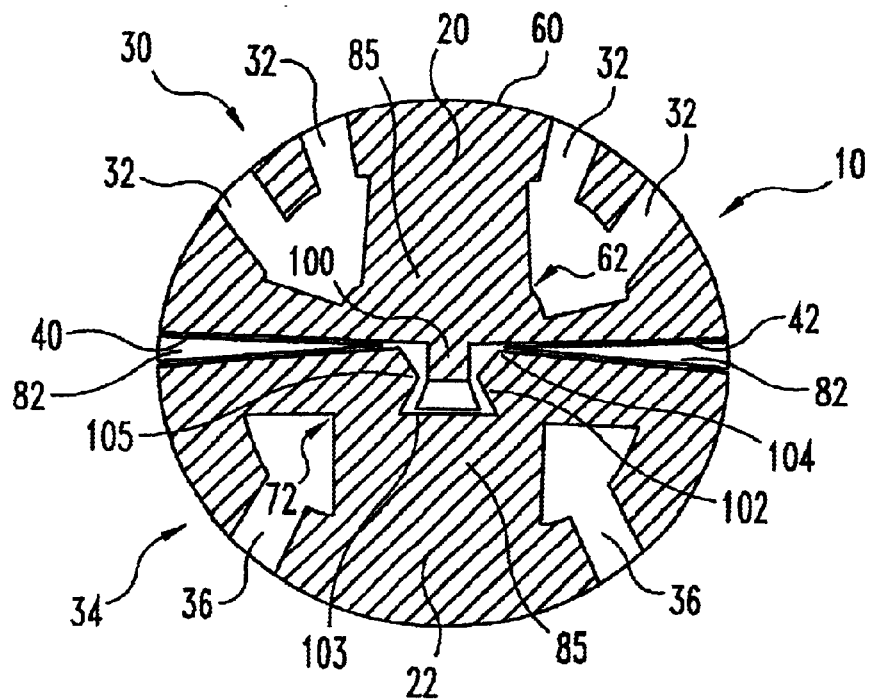
FIG. 9 shows a cross-sectional end view of a spinal implant with a hour-glass shaped rocker and a hour-glass shaped channel articulating means.

In an alternative to this embodiment, as shown in FIG. 9, a second range of motion can be added to the articulating means 24 by modifying the shape of the channel 102. The modified channel 102 can be, for example, substantially hour-glass in shape through the depth of the channel 102. The channel width at the channel's base 103 and mouth 104 are greater then the channel width at the channel's midpoint 105. The hour-glass shaped channel 102 permits a tilting motion along two perpendicular linear planes.

Figure 11A:
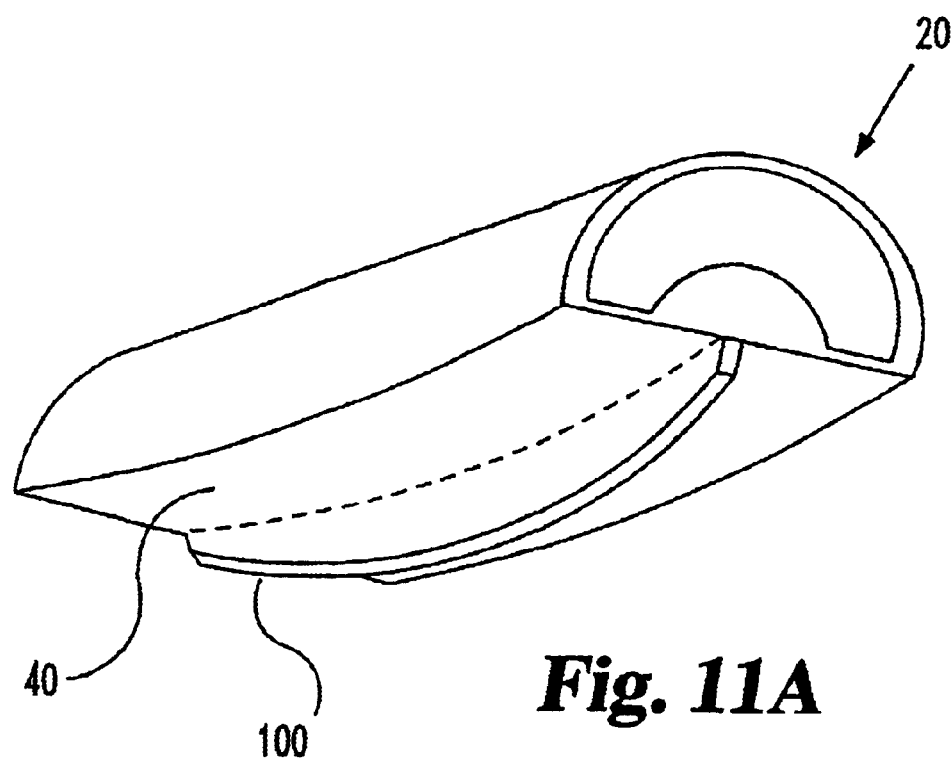
FIGS. 11a & 11b show a perspective view of a spinal implant with a rocker and alternative hour-glass channel articulating means.
Figure 11B:
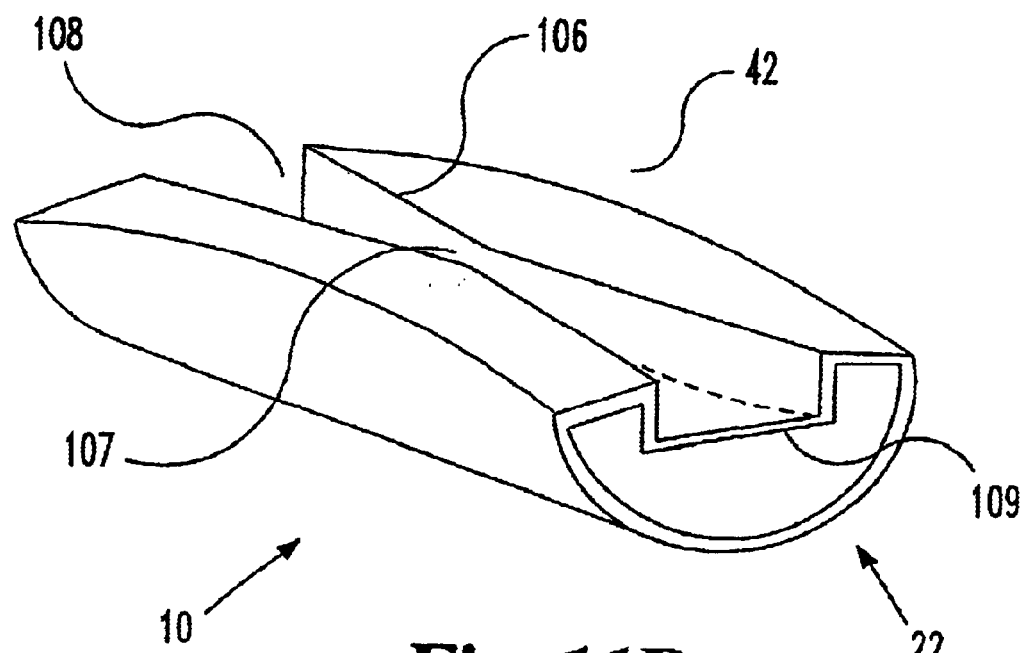

In a second alternative to this embodiment, as shown in FIGS. 11a and 11b, an alternative second range of motion can be added to the articulating means 24 by modifying the shape of the channel 101. The modified channel 106 can be, for example, substantially hour-glass in shape through the length of the second element 22. The channel width at the channel's longitudinal midpoint 107 is less than the channel width at the channel's leading end 108 and tail end 109. Those skilled in the art, having the benefit of the instant disclosure, will appreciate that the "hour-glass" shape as described herein includes various curves or straight edges so long as the width at, or near, the end points of the channel (or the top and bottom of the channel) is wider than the width at some point between the end points. The hour-glass shaped channel 106 permits two ranges of motion, a tilting motion and a pivoting motion, about the central axis. These motions may be desirable for some patients.

Figure 15A:
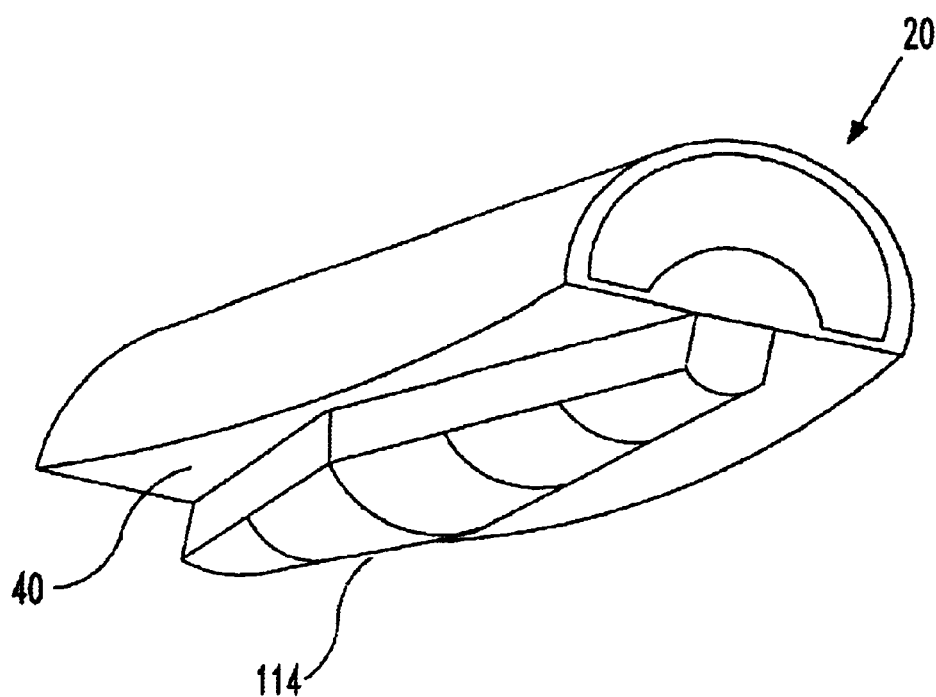
FIGS. 15a & 15b show a perspective view of a spinal implant with an alternative diamond shaped channel and corresponding diamond shaped rocker articulating means.
Figure 15B:
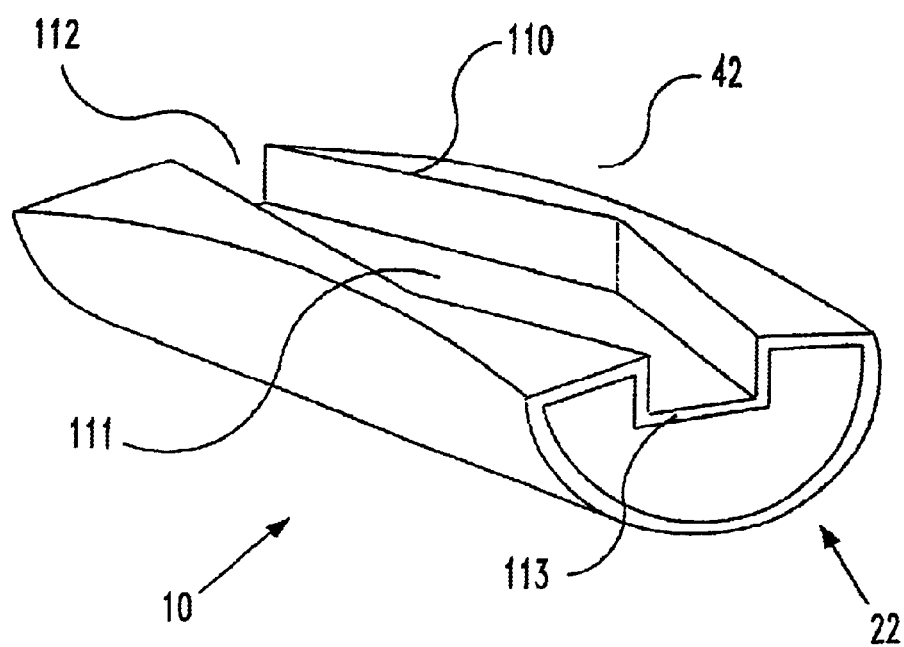

In a third alternative to this embodiment, as shown in FIGS. 15a and 15b, an alternative second range of motion can be added to the articulating means 24 by modifying the shape of the channel 101. The modified channel 110 can be, for example, substantially diamond in shape through the length of the second element 22. The channel width at the channel's longitudinal midpoint 111 is greater than the channel width at the channel's leading end 112 and tail end 113. Additionally, the first articulation surface 40 comprises a correspondingly-shaped rocker 114 which can be, for example, diamond in shape along the length of the first element 20. Those skilled in the art, having the benefit of the instant disclosure, will appreciate that the "diamond" shape as described herein includes various curves or straight edges so long as the width at some point between the end points of the channel (or the top and bottom of the channel) is wider than the width at, or near, the end points. The diamond shaped channel 110 permits three ranges of motion, a tilting motion and a pivoting motion, about the central axis. These motions may be desirable for some patients.

The channel's 101 articulating surface may be planar, concave or convex, as may be required to duplicate physiologic spinal articulation. It is also noted that the articulating means 24 can be in an opposite configuration as previously disclosed, where the first articulation surface 40 comprises a substantially U-shaped channel 101 extending along the length of the first element 20, and the second articulation surface 42 comprises a correspondingly-shaped rocker 100 along the length of the second element 22, where such opposite configuration does not materially affect the function of the subject invention.

The articulation means 24 preferably further comprises one or more angularly offset bevels 50 formed in the first internal articulation surface 40 and/or the second internal articulation surface 42, to allow relative tilting movement between the first and second vertebra 12, 14 in one or more directions. According to the embodiment shown in the figures, the first and second internal articulation surfaces 40, 42 are each provided with an angularly offset bevel 50, in a generally pyramidal configuration, as seen best in FIG. 1, thereby enabling tilting movement in all directions (360°). A generally conical configuration is also possible and, likewise, would permit both rotational movement and 360° tilting movement. Additionally, as shown in FIGS. 10 and 11, the first and second articulating surfaces 40, 42 can each be provided with a general arc configuration, which provide a greater range of motion.

The natural range of motion of the spine may be approximated by providing bevels 50 of approximately 5° around the periphery of each of the first and second articulation surfaces 40,42, thereby allowing approximately 10° of tilt in all directions between adjacent vertebra. As depicted in the figures, the pivot point or axis of the articulation means 24 is generally centrally located on the first and second articulation surfaces 40, 42, and will be aligned with the spine's normal axis of rotation when implanted as shown in FIG. 4. This location, however, can be selectively varied to position the center of rotation of the articulation means 24 centrally, anteriorly, posteriorly, to the left, to the right, or eccentrically (off-center in both the anterior/posterior direction and the left/right direction) of the spine's normal axis of rotation, in order to achieve proper alignment of the spine, thereby restoring optimal sagittal and coronal spinal balance and alignment.

In one embodiment as shown best by FIGS. 1–3, the first and second elements 20, 22 of the implant 10 of the present invention, preferably comprise generally hemi-cylindrical outer walls 60, 70 adjoining to form a generally cylindrical body. When in their assembled configuration, the first element 20 and the second element 22 abut one another with their respective first and second articulating surfaces 40, 42 adjacent and engaging one another, as described above. The first element 20 preferably further comprises a first radiused outer wall 60. The one or more openings 32 for facilitating bone ingrowth are provided in this first radiused outer wall 60, and communicate with a first fusion chamber 62 formed between the first radiused outer wall 60 and the first articulating surface 40. Similarly, the second element 22 preferably comprises a second radiused outer wall 70, defining one or more openings 36 for facilitating bone ingrowth. The openings 36 communicate with a second fusion chamber 72 formed between the second radiused outer wall 70 and the second articulating surface 34. The first and second radiused outer walls 60, 70 can be provided with threads 80 to facilitate advancing the implant 10 into the intervertebral space during implantation and to help secure the implant 10 in position once implanted. The threads 80 on each of the first and second radiused outer walls 60, 70 are preferably aligned to form continuous threads when the first and second elements 20, 22 are engaged. In some instances, it may be desirable to provide self-tapping threads 80, and/or to configure the threads 80 to direct bone fragments generated by implantation into the openings 32, as taught by U.S. Pat. No. 5,489,308 to Kuslich, et al. In other less preferred embodiments, the threads 80 can be replaced with a contoured outer surface comprising smooth, splined, flanged, spiked or beaded surface features. The implant 10 can further comprise one or more support flanges 85 in the first and/or second elements 20, 22, for additional strength.

Figure 12:
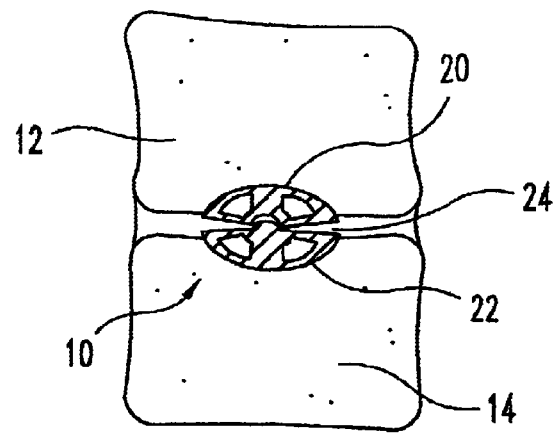
FIG. 12 is an end view of a spinal implant in-situ according to the elliptical form of the present invention.

In a second embodiment as shown best by FIGS. 6a, 6b and 12, the first and second elements 20, 22 of the implant 10 of the present invention preferably comprise hemi-elliptical outer walls 97, 99 adjoining to form an elliptical body. When in their assembled configuration, the first element 20 and the second element 22 abut one another with their respective first and second articulating surfaces 40, 42 adjacent and engaging one another, as described above. The first element 20 preferably further comprises a first radiused outer wall 97. The one or more openings 32 for facilitating bone ingrowth are provided in this first radiused outer wall 97, and communicate with a first fusion chamber 62 formed between the first radiused outer wall 97 and the first articulating surface 40. Similarly, the second element 22 preferably comprises a second radiused outer wall 99, defining one or more openings 36 for facilitating bone ingrowth. The openings 36 communicate with a second fusion chamber 72 formed between the second radiused outer wall 99 and the second articulating surface 42. In alternative embodiments the contoured outer surfaces of the first and second elements 20, 22 can comprise smooth, splined, flanged, spiked or beaded surface features to secure the element in position once implanted. The implant 10 can further comprise one or more support flanges 85 in the first and/or second elements 20, 22, for additional strength.

Figure 13:
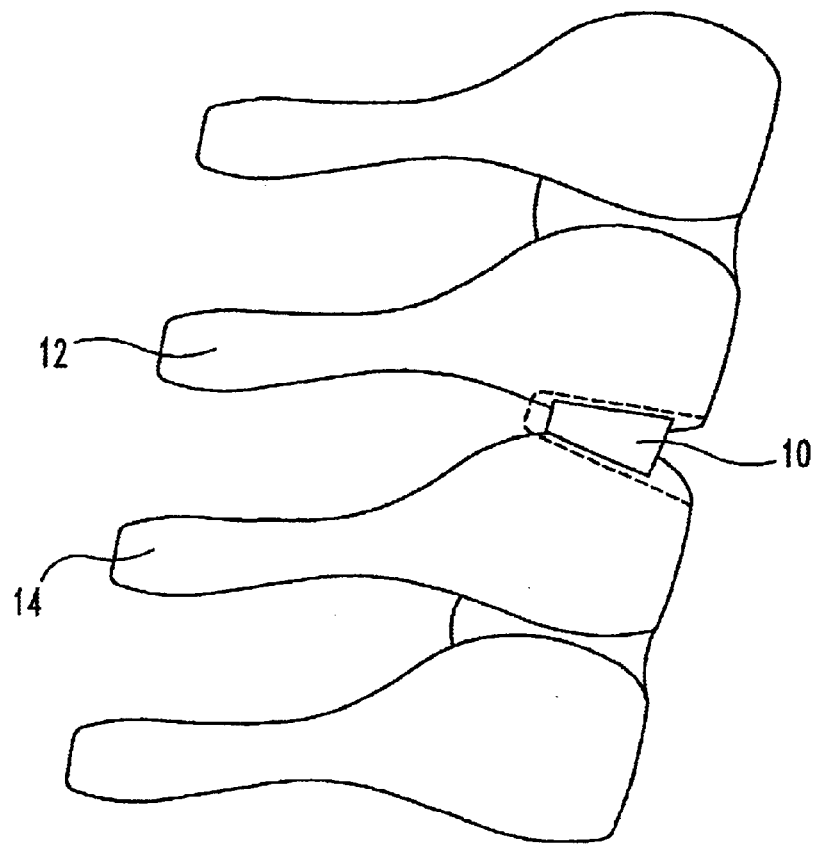
FIG. 13 is a side view of a spinal implant in-situ according to the tapered form of the present invention.

In another embodiment, as shown in FIGS. 7 and 13, the element 10 may be tapered along the horizontal axis. The tailing end 92 has a vertical radius greater than the vertical radius of the leading end 93. The tapered shape decreases the amount of material required to be removed and increases the ease of insertion of the implant 10 in between the first and second vertebra.

In still further embodiments, the spinal implant 10 may have a first and second element for affixing the spinal implant 10 to a first and second vertebra in the shape of a rectangular, plate or any of the affixing means as disclosed in the following: U.S. Pat. No. 4,759, 769, to Hedman, et al., U.S. Pat. No. 4,946,378, to Hirayama, et al., U.S. Pat. No. 4,997,432, to Keller, U.S. Pat. No. 5,002,576, to Fuhrmann, et al., U.S. Pat. No. 5,236,460, to Barber, U.S. Pat. No. 5,258,031, to Salib, et al., U.S. Pat. No. 5,306,308, to Gross, et al., U.S. Pat. No. 5,401,269, to Buttner-Janz, et al., U.S. Pat. No. 5,425,773, to Boyd, et al., and U.S. Pat. No. 5,782,832, to Larsen, et al.

In a further preferred embodiment. As shown in FIGS. 2–3, the present invention may further comprise the provision of one or more stabilizing means for temporarily rigidly coupling the first element 20 to the second element 22 to prevent relative movement there between, for example, it is preferred that the first and second elements 20, 22 be held rigidly in place during installation of the implant 10 into the intervertebral space. In addition, the first and second elements 20, 22 should remain rigidly coupled for a sufficient length of time after implantation to permit sufficient bone ingrowth into the fusion chambers to prevent relative motion between the implant 10 and the vertebra 12, 14 during normal activities of the patient. Typically, approximately eight to twenty weeks of bone ingrowth will be sufficient, before the first and second elements 20, 22 are uncoupled and permitted to articulate relative to one another. This temporary stabilization of the first and second elements is accomplished by the present invention, without the requirement of a second surgical procedure, through the use of medium-term stabilizing means formed from bioreabsorbable material. Examples of bioreabsorbable materials include polyglycolate polymers or analogues, lactides, polydioxanone, polyglyconate, lactide/glycolide copolymers. By appropriate selection of the material(s) of construction, the length of time required to biodegrade the stabilizing means can be effectively controlled. After the stabilizing means are dissolved and absorbed by the body, the first and second elements of the implant 10 are uncoupled, allowing articulation. In one example embodiment, depicted in FIG. 3, the stabilizing means can comprise one or more biodegradable shims 82 wedged between the first element 20 and the second element 22, to prevent relative motion there between. In another example embodiment, the first and second elements 20, 22 are placed in their coupled configuration, as shown in FIGS. 2–3, with the spaces between the articulating surfaces 40, 42, then being injected or filled with a biodegradable polymer, which provides the medium term temporary stabilizing means to couple the elements in position. Care will be taken to avoid filling the fusion chambers 30, 34 and the openings 32, 36 to the fusion chambers with the polymer, which could inhibit bone ingrowth. The threads 80 will also remain exposed to assist in implantation of the device. In another example embodiment, depicted in FIG. 2, the stabilizing means comprise a removable and/or bioreabsorbable endcap 90, which releasably engages the tailing end 92 of the implant 10 to couple the first and second elements 20, 22. The endcap can comprise one or more clips 94 for engaging the implant 10, and one or more keyways 96 for engaging a wrench, driver or other actuation device used to advance the implant 10 into the intervertebral space. A second removable and/or absorbable endcap can be installed on the leading end 93 of the implant 10. The endcaps may additionally function to retain the bone fragments within the chambers 62, 72 of the fusion chambers 30, 34, as will be described in greater detail below, until sufficient bone ingrowth and fusion has occurred.

Another embodiment of the present invention is depicted by FIG. 5, which shows an implant 10, generally comprising first and second elements 20, 22, substantially as described above, and further comprising an intermediate articulation element, which in the depicted embodiment comprises a generally hemispherical bowl-shaped cap 90 interposed between the concave surface 46 of the first element 20 and the convex surface 48 of the second element 22. The cap 90 is preferably fabricated from a wear-resistant, low friction material of construction, which may be somewhat resilient to absorb impact loading. The provision of the cap 90 allows articulation at the interface between the top surface of the cap and the concave surface 46 of the first element 20, and between the bottom surface of the cap and the convex surface 48 of the second element 22, resulting in a bipolar articulation. This arrangement reduces frictional wear on the articulation surfaces by distributing wear over two articulation interfaces. The engagement of the concave lower surface of the cap 90 with the convex surface 48 of the second element 22, and the engagement of the convex upper surface of the cap 90 with the concave surface 46 of the first element 20, prevents the cap 90 from becoming dislodged when the implant 10 is installed.

The present invention further comprises a method of maintaining a desired intervertebral space between a first vertebra 12 and a second vertebra 14. The method preferably comprises removing a section of the first vertebra to form a cavity therein, mounting a first element of an articulating spinal implant into the cavity, and connecting a second element of the implant to the second vertebra. The articulating spinal implant used to carry out this method is preferably substantially similar to the example embodiment described above, having first and second internal articulation surfaces which adjoin to form a joint allowing relative pivotal movement between the first and second elements, but preventing relative axial compression there between. At least one of the elements preferably further comprises a fusion chamber, including a chamber and at least one opening communicating with the chamber, for facilitating bone ingrowth into, through, and around the fusion chamber from the respective vertebra. In a preferred form, the method of the present invention comprises attachments of both the first and second elements of the implant to the respective vertebra using fusion chambers for bone ingrowth. In this embodiment, a section of the second vertebra is preferably removed to form a cavity therein for receiving the second element of the implant. The method of the present invention can further comprise the insertion of bone fragments, which may be the fragments formed in the above-described removal of vertebral sections, into the fusion chamber(s) of the implant. The presence of these bone fragments has been shown to stimulate and enhance bone ingrowth into the fusion chamber. In another embodiment, the method of the present invention anticipates the application of means for stimulating bone growth into, through, and/or around the fusion chamber(s). The means for stimulating bone growth can comprise, for example, electrical or magnetic bone growth stimulators, bone morphogenetic protein (BMP), hydroxyl apatite compounds, demineralized bone compound, and/or other bone growth stimulating devices or compounds. It is also anticipated that the introduction of a cyanoacrylate material, commonly referred to as surgical glue, onto the outer surface of the fusion chamber(s) may be used to fix the implant in optimal position awaiting bone ingrowth.

Implantation of the articulating spinal implant, according to the present invention, may be carried out in a manner generally similar to previously-known methods for the implantation of non-articulating, rigid-fusion implants, with exceptions as set out herein, for example, the method of the present invention may utilize standard surgical approaches to the spine from either an anterior approach for the cervical and thoracic spinal segments, or from an anterior or posterior lateral approach to the lumbar spinal segments. The removal of vertebral sections may be accomplished by drilling or chipping a generally circular bore having a diameter and depth adapted to generally match the implant to be utilized, bridging the first and second vertebra. Additionally, the circular bore may be tapered with the leading end diameter being smaller then the tail end diameter. The bore is preferably centered over the intervertebral space, approximately midway between the first and second vertebra. Threads may then be tapped into the bore to facilitate insertion of the implant.

Figure 14A:
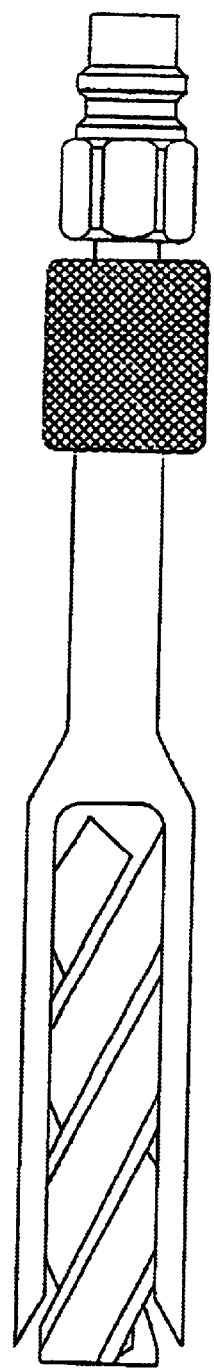
FIG. 14a shows a side view of surgical instrument for cutting an elliptical section in between spinal vertebra.
Figure 14B:
FIG. 14b shows a bottom view of surgical instrument for cutting an elliptical section in between spinal vertebra.

In an alternative method, the removal of vertebral sections may be accomplished by using an unique surgical instrument, as shown in FIGS. 14a and 14b, for drilling an elliptical bore having a major and minor diameter and depth adapted to generally match the implant to be utilized, bridging the first and second vertebra. Preferably, the surgical instrument is affixed to a drill to provide rotational power to the cutting portion. The cutting portion of the surgical instrument consists of a circular flute drill bit sheathed within cutting blades formed in an elliptical shape. The flute drill bit extends out beyond cutting blades to cut a circular section between the first and second vertebra. As the drill bit cuts into the vertebra, the cutting blades then remove the remaining material to form an elliptical bore having a major and minor diameter and depth adapted to generally match the implant to be utilized, bridging the first and second vertebra.

Alternatively, the implant can be provided with self-tapping threads. The implant is assembled with the first and second articulating surfaces engaged, and the first and second elements of the implant are rigidly coupled by stabilizing means substantially as described above. The stabilized implant is advanced into the bore to the desired depth. Preferably, the implant is advanced until the tailing end 92 is flush or slightly recessed relative to the outer surface of the vertebra, thereby eliminating the possibility that outwardly projecting portions of the implant may interfere with or injure adjacent or regional vascular, neural or visceral structures.

In the lumbar area, where greater load bearing is required, two articulating implants can be placed in parallel positions with the lengthwise axis of each adjacent one to the other, in a generally parallel arrangement, allowing flexion/extension movement alone. This arrangement will typically require removal of vertebral material to form two openings, or an extended opening to accommodate both implants. Alternatively, a single, appropriately sized implant could be placed in the interspace utilizing the transabdominal open surgical approach, the transabdominal laparoscopic approach, or the retroperitoneal open anterior approach allowing pivotal motion around the single point of articulation as described above for use in cervical and thoracic intervertebral disc spaces.

Post-operatively, bone ingrowth will occur, fusing the first and/or second elements of the implant to the respective vertebra. After sufficient passage of time, the stabilizing means is dissolved and absorbed into the body, uncoupling the articulation means to permit relative motion between the first and second elements, thus preserving spinal flexibility and minimizing destructive stress upon adjacent intervertebral joints. The implant resists axial compression between the first and second elements, thereby preventing relative compression between the first and second vertebra, thus maintaining the desired intervertebral space. Further, the implant is recessed into the recipient vertebral site, eliminating impingement on the next adjacent vascular, neural or visceral structures.

While the invention has been disclosed in its preferred forms, it will be apparent to those skilled in the art that many modifications, additions, and deletions can be made therein without departing from the spirit and scope of the invention and its equivalents as set forth in the following claims.

REFERENCES

Van C. Mow and Wilson C. Hayes, *Basic Orthopaedic Biomechanics*, $2^{nd}$ *Edition*, (Lippincott-Raven Publisher) (1997).

Augustus A. White III and Manohar M. Panjabi, *Biomechanics of the Spine*, $2^{nd}$ *Edition*, (Lippincott-Raven Publisher) (1990).

René Louis, *Surgery of the Spine, Surgical Anatomy and Operative Approaches*, (Springer-Verlay Berlin Heidelberg New York) (1983)

Josef Pospiech, M.D., Dietmer Stolke, M.D., Hans J. Wilke, Ph.D., Lutz E. Claes, Ph.D., *Intradiscal Pressure Recording in the Cervical Spine*, Neurosurgery, Vol 44, No. 2, 379 (February 1999).

What is claimed is:

1. A spinal implant, comprising:
    an articulating means positionable between a first vertebra and a second vertebra, wherein said articulating means permits an articulation of said first vertebra and said second vertebra about an instantaneous axis of rotation;
    a first element comprising a first articulating surface and a first connection means for engaging said first vertebra; and
    a second element comprising a second articulating surface and a second connection means for engaging said second vertebra; and
    wherein said first articulating surface abuts said second articulating surface to form said articulating means; and
    wherein said articulating means comprises a channel along a length of said second element and a rocker along a length of said first element, at least a portion of said rocker engaged within said channel, said channel along the length of said second element having a channel width at a leading end and a tail end which is greater than the channel width at some point between said leading end and said tail end; and
    whereby said articulation of said first vertebra and said second vertebra is substantially similar to the biomechanical motion of a substantially identical pair of adjacent vertebrae interacting with a natural intervertebral disc.

2. A spinal implant, comprising:
    an articulating means positionable between a first vertebra and a second vertebra, wherein said articulating means permits an articulation of said first vertebra and said second vertebra about an instantaneous axis of rotation;
    a first element comprising a first articulating surface and a first connection means for engaging said first vertebra; and
    a second element comprising a second articulating surface and a second connection means for engaging said second vertebra; and
    wherein said first articulating surface abuts said second articulating surface to form said articulating means; and
    wherein one of said first and second articulating surfaces is a convex surface, and wherein another of said first and second articulating surfaces is a substantially planar surface; and
    whereby said articulation of said first vertebra and said second vertebra is substantially similar to the biomechanical motion of a substantially identical pair of adjacent vertebrae interacting with a natural intervertebral disc.

3. The spinal implant according to claim 2, wherein said articulation of said first vertebra and said second vertebra is a rotation about said instantaneous axis of rotation.

4. The spinal implant according to claim 3, wherein said articulation of said first vertebra and said second vertebra is a rotation in the sagittal plane.

5. The spinal implant according to claim 3, wherein said articulation of said first vertebra and said second vertebra is a rotation in the frontal plane.

6. The spinal implant according to claim 3, wherein said articulation of said first vertebra and said second vertebra is a rotation in the horizontal plane.

7. The spinal implant according to claim 3, wherein said articulation of said first vertebra and said second vertebra is a rotation in the sagittal, frontal and horizontal planes.

8. The spinal implant according to claim 2, wherein said articulation of said first vertebra and said second vertebra is a paradoxical motion.

9. The spinal implant according to claim 8, wherein said articulation of said first vertebra and said second vertebra is a paradoxical motion in the sagittal plane.

10. The spinal implant according to claim 8, wherein said articulation of said first vertebra and said second vertebra is a paradoxical motion in the frontal plane.

11. The spinal implant according to claim 8, wherein said articulation of said first vertebra and said second vertebra is a paradoxical motion in the horizontal plane.

12. The spinal implant according to claim 8, wherein said articulation of said first vertebra and said second vertebra is a paradoxical motion in the sagittal, frontal and horizontal planes.

13. The spinal implant according to claim 2, wherein said articulating means is positionable within an intervertebral space between the first and second vertebrae such that said instantaneous axis of rotation is disposed in an area outside of the intervertebral space.

14. The spinal implant according to claim 2, wherein said one of said first and second articulating surfaces has a hemi-elliptical shape.

15. A spinal implant adapted for insertion within an intervertebral space between adjacent vertebrae, comprising:

a first element having a first articulation surface; and a second element having a second articulation surface;

said first and second articulation surfaces cooperating to provide articulation between the adjacent vertebrae about an instantaneous axis of rotation to restore substantially normal bio-mechanical motion of the adjacent vertebrae; and wherein one of said first and second articulation surfaces is a convex surface and another of said first and second articulation surfaces is a substantially planar surface.

16. The spinal implant according to claim 15, wherein said instantaneous axis of rotation is disposed in an area outside of the intervertebral space.

17. The spinal implant according to claim 15, wherein said convex surface has a hemi-elliptical shape.

18. The spinal implant according to claim 15, wherein said first articulation surface extends along substantially an entire dimension of said first element, and wherein said second articulation surface extends along substantially an entire dimension of said second element.

19. The spinal implant according to claim 15, wherein one of said first and second articulation surfaces is defined by an elongate rocker and wherein another of said first and second articulation surfaces is defined by an elongate channel, said elongate rocker cooperating with said elongate channel to provide said articulation between the adjacent vertebrae.

20. The spinal implant according to claim 19, wherein said elongate channel has a U-shape.

21. The spinal implant according to claim 19, wherein said elongate channel has a varying channel width.

22. The spinal implant according to claim 15, wherein said articulation between the adjacent vertebrae is rotational motion about said instantaneous axis of rotation.

23. The spinal implant according to claim 15, wherein said first and second articulation surfaces cooperate to provide paradoxical motion between the adjacent vertebrae.

24. The spinal implant according to claim 23, wherein said paradoxical motion is paradoxical rotational motion between the adjacent vertebrae.

25. The spinal implant according to claim 23, wherein said paradoxical motion is paradoxical sliding motion between the adjacent vertebrae.

26. A spinal implant adapted for insertion within an intervertebral space between adjacent vertebrae, comprising:

a first element having a first articulation surface; and a second element having a second articulation surface;

said first and second articulation surfaces cooperating to provide articulation between the adjacent vertebrae about an instantaneous axis of rotation to restore substantially normal bio-mechanical motion of the adjacent vertebrae; and wherein one of said first and second articulation surfaces is defined by an elongate rocker and wherein another of said first and second articulation surfaces is defined by an elongate channel, said elongate rocker cooperating with said elongate channel to provide said articulation between the adjacent vertebrae, said elongate channel having a varying channel width and having an hourglass shape.

27. The spinal implant according to claim 26, wherein said rocker has a hemi-elliptical shape.

* * * * *